United States Patent
Chen et al.

(10) Patent No.: US 10,905,830 B2
(45) Date of Patent: Feb. 2, 2021

(54) AUTOMATIC INJECTION DEVICE FOR FLUID

(71) Applicant: BANZA STAMPING INDUSTRY CORP., Su'ao Township, Yilan County (TW)

(72) Inventors: Li-Wei Chen, Su'ao Township, Yilan County (TW); Cole Krebs, Su'ao Township, Yilan County (TW)

(73) Assignee: BANZA STAMPING INDUSTRY CORP., Suao Township (TW)

( * ) Notice: Subject to any disclaimer, the term of this patent is extended or adjusted under 35 U.S.C. 154(b) by 288 days.

(21) Appl. No.: 16/005,885

(22) Filed: Jun. 12, 2018

(65) Prior Publication Data

US 2019/0374718 A1 Dec. 12, 2019

(51) Int. Cl.
*A61M 5/20* (2006.01)
*A61M 5/32* (2006.01)
*A61M 5/46* (2006.01)
*A61M 5/31* (2006.01)

(52) U.S. Cl.
CPC ........ *A61M 5/2053* (2013.01); *A61M 5/3202* (2013.01); *A61M 5/46* (2013.01); *A61M 5/3129* (2013.01); *A61M 2005/206* (2013.01)

(58) Field of Classification Search
CPC .... A61M 5/2053; A61M 5/3202; A61M 5/46; A61M 2005/206; A61M 5/3129; A61M 5/30; A61M 5/2033
See application file for complete search history.

(56) References Cited

U.S. PATENT DOCUMENTS 2,680,439 A * 6/1954 Sutermeister ........... A61M 5/30
604/70
2017/0290982 A1 10/2017 Edwards et al.

FOREIGN PATENT DOCUMENTS

CN 87105155 A 1/1988
TW 200303224 A 9/2003

* cited by examiner

*Primary Examiner* — Theodore J Stigell
*Assistant Examiner* — Daniel Moore
(74) *Attorney, Agent, or Firm* — patenttm.us

(57) ABSTRACT

An automatic injection device for fluid has a sleeve, an actuating unit, a barrel with a piercing needle, a high-pressure air source and a driven unit. The actuating unit is mounted in the sleeve. The high-pressure air source and the driven unit are mounted slidably in the barrel. The barrel, the high-pressure air source and the driven unit are first mounted in the sleeve to be ready for use. When the user needs to release the high-pressure air in the high-pressure air source, the user press the actuating unit to drive the driven unit to slide. Then the driven unit also drives the high-pressure air source to slide until the high-pressure air source hits the piercing needle. Therefore, the high-pressure air in the high-pressure air source is easily released by actuate the actuating unit without additional hand tools.

7 Claims, 23 Drawing Sheets

US 10,905,830 B2

AUTOMATIC INJECTION DEVICE FOR FLUID

BACKGROUND OF THE INVENTION

1. Field of the Invention

The present invention is an automatic injection device, specifically an automatic injection device for fluid.

2. Description of the Prior Arts

Pneumatic devices usually comprise a high-pressure air source therein to be actuated to instantly release the high pressure air to pushes the liquid out. The high-pressure air source is sealed before being assembled in the pneumatic device. After the high-pressure air source is assembled in the pneumatic device, the user needs to use a hand tool to unseal the high-pressure air source so that the compressed air in the high-pressure air source could come out to pushes the liquid out. However, using the hand tool to unseal the high-pressure air source is inconvenient for the user, especially for pneumatic medical device.

To overcome the shortcomings, the present invention provides an automatic injection device for fluid to mitigate or to obviate the aforementioned problems.

SUMMARY OF THE INVENTION

The objective of the present invention is to provide an automatic injection device for fluid to allow easily use. The automatic injection device for fluid has a sleeve, an actuating unit, a barrel with a piercing needle, a high-pressure air source and a driven unit. The actuating unit is mounted in the sleeve. The high-pressure air source and the driven unit are mounted slidably in the barrel. The barrel, the high-pressure air source and the driven unit are first mounted in the sleeve to be ready for use. When the user needs to release the high-pressure air in the high-pressure air source, the user press the actuating unit to drive the driven unit to slide. Then the driven unit also drives the high-pressure air source to slide until the high-pressure air source hits the piercing needle. Therefore, the high-pressure air in the high-pressure air source is easily released by actuate the actuating unit without additional hand tools. Other objectives, advantages and novel features of the invention will become more apparent from the following detailed description when taken in conjunction with the accompanying drawings.

DETAILED DESCRIPTION OF THE EMBODIMENTS

Figure 1:
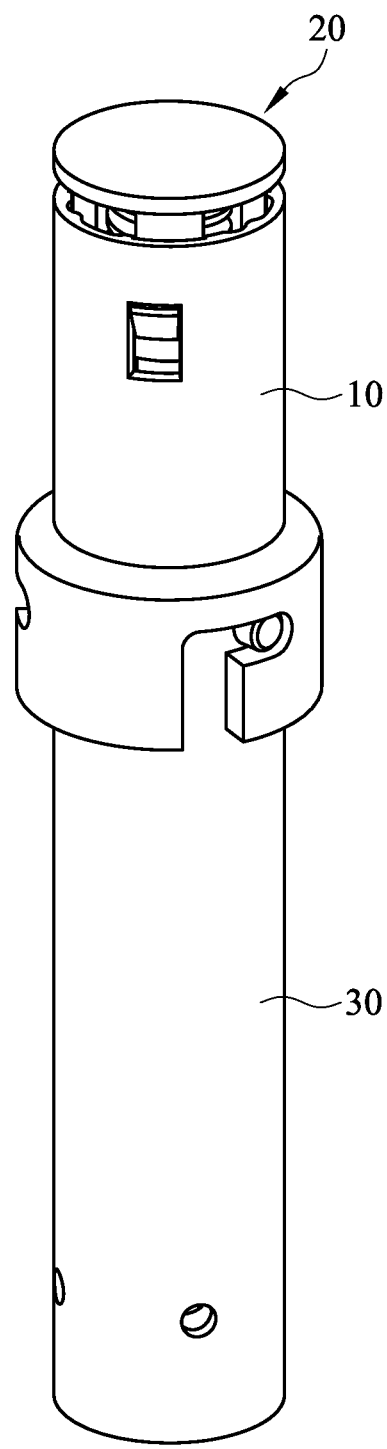
FIG. 1 is a perspective view of an automatic injection device for fluid in accordance with the present invention.
Figure 2:
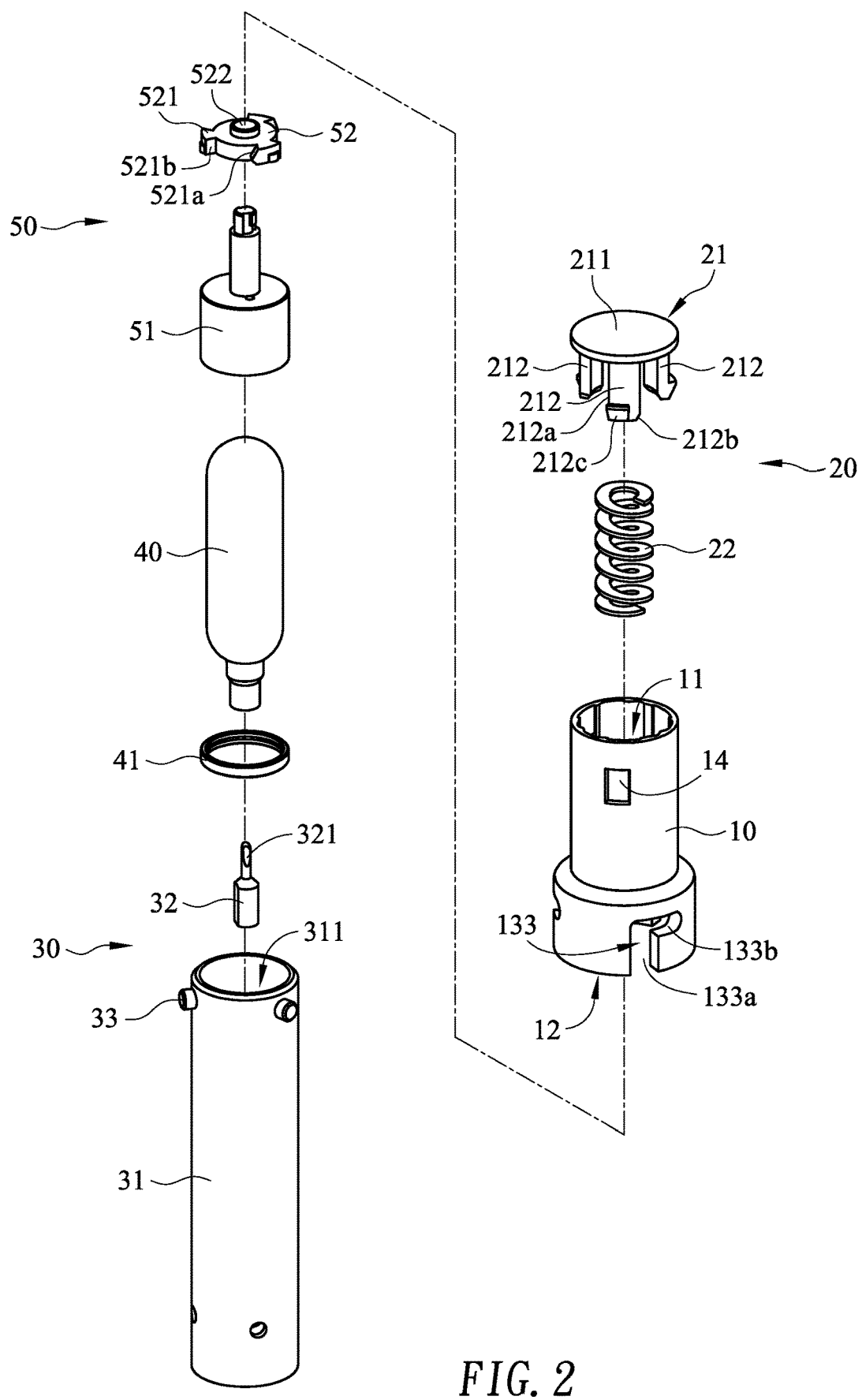
FIG. 2 is an exploded perspective view of the automatic injection device for fluid in FIG. 1.

With reference to FIGS. 1 and 2, an automatic injection device for fluid in accordance with the present invention comprises a sleeve 10, an actuating unit 20, a barrel 30, a high-pressure air source 40 and a driven unit 50.

Figure 3:
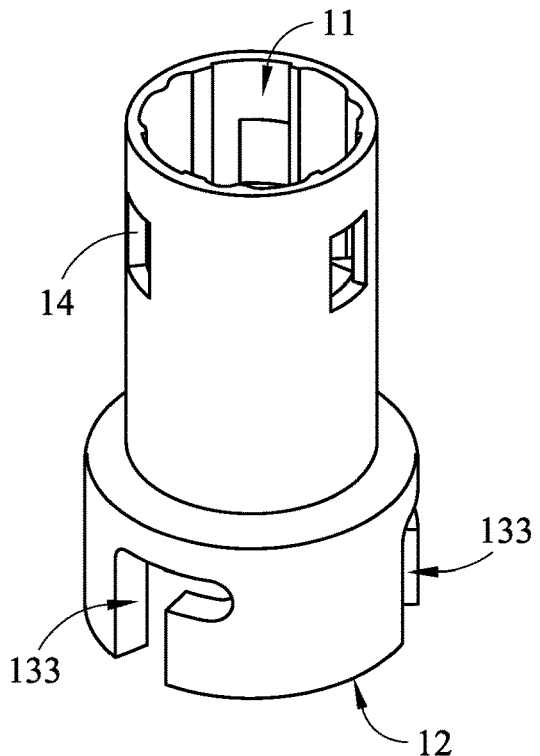
FIG. 3 is a perspective view of the sleeve of the automatic injection device for fluid in FIG. 1.
Figure 4:
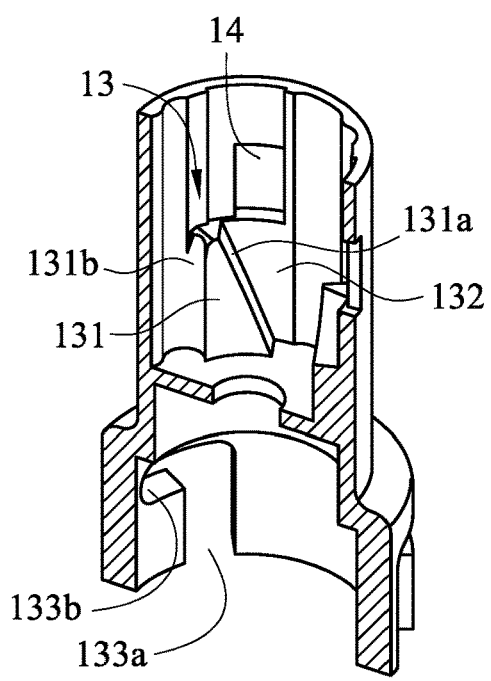
FIG. 4 is a cross-sectional perspective view of the sleeve of the automatic injection device for fluid in FIG. 1.

With reference to FIGS. 2 to 4, the sleeve 10 is hollow and has an inside wall, a first end opening 11, a second end opening 12, a limiting unit 13 and multiple optional windows 14. The limiting unit 13 is attached to the sleeve 10 and may comprise multiple stops 131, multiple passages 132 and multiple lock holes 133. The stops 131 are formed separately on the inside wall of the sleeve 10. Each stop 131 has an inclined side 131a and an upright side 131b. Each passage 132 is formed on the inside wall of the sleeve 10 and is formed between adjacent stops 131 to separate the stops 131. The lock holes 133 are formed transversely through the sleeve 10. Each lock hole 133 has a longitudinal part 133a and a lateral part 133b communicating with the longitudinal part 133a. The longitudinal part 133a of each lock hole 133 communicates with the second end opening 12 of the sleeve 10. The windows 14 are formed transversely through the sleeve 10. In one embodiment, each window 14 corresponds to one of the passage 132.

Figure 5:
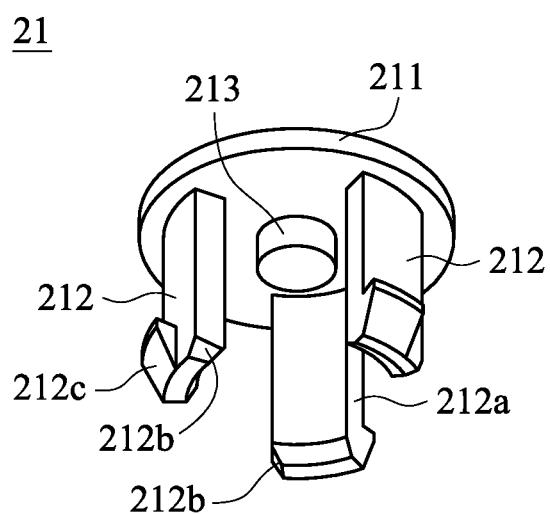
FIG. 5 is a perspective view of the actuating cap of the automatic injection device for fluid in FIG. 1.

With reference to FIGS. 2, 4 and 5, the actuating unit 20 is mounted through the sleeve 10 and may comprise an actuating cap 21 and a resilient element 22. The actuating cap 21 is mounted movably through the first end opening 11 of the sleeve 10 and has a base 211, multiple claws 212 and a bump 213. The claws 212 are formed longitudinally on the base 211 and separate to each other. Each claw 212 corresponds to one of the passage 132 and has a free end, a first side, a second side, an outer side, a flat surface 212a, an inclined surface 212b and a tab 212c. The outer side is defined between the first and second sides. The flat surface 212a is formed on the first side of the claw 212. The inclined surface 212b is formed on the second side of the claw 212 and connects to the free end of the claw 212. The tab 212c is formed on outer side of the claw 212 and is mounted through one of the windows 14 of the sleeve 10 to limit the sliding route of the actuating cap 21. The bump 213 is formed longitudinally on the base 211 and may be formed at a center of the base 211. The resilient element 22 is mounted in the sleeve 10 and is pressed against the actuating cap 21. In one embodiment, one end of the resilient element 22 is mounted around the bump 213 of the actuating cap 21. The resilient element 22 may be a spring.

Figure 6:
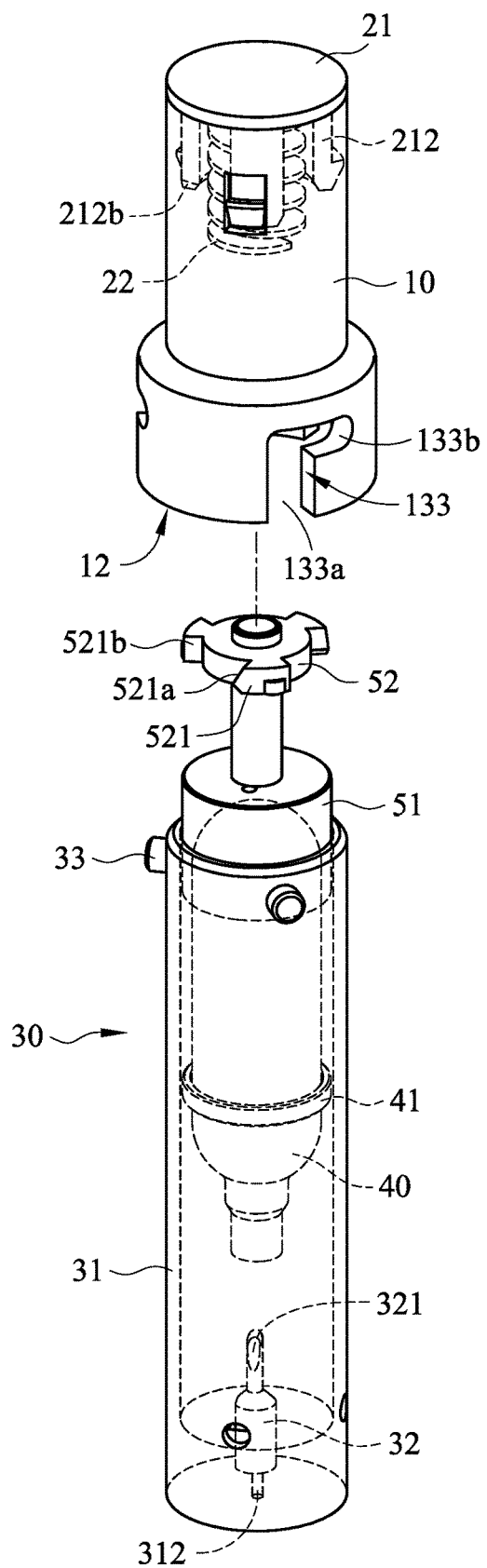
FIG. 6 is an operational perspective view of the automatic injection device for fluid in FIG. 1, showing that the barrel is not yet inserted into the sleeve.
Figure 7:
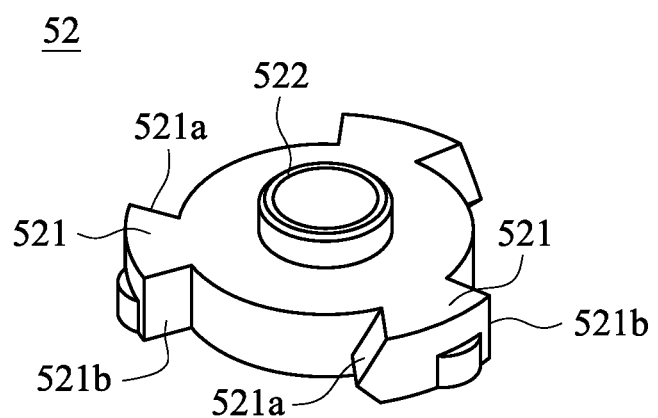
FIG. 7 is a perspective view of the cam of the automatic injection device for fluid in FIG. 1.

With reference to FIGS. 2 and 6, the barrel 30 is selectively held on the second end opening 12 of the sleeve 10 and may comprise a body 31, a piercing needle 32 and multiple protruding parts 33. The body 31 is hollow and has an inside wall, an outside wall, a first end opening 311, a second end and a slot 312. The slot 312 is formed through the second end of the body 31. The piercing needle 32 is attached to the second end of the body 31 and may have a central hole 321 communicating with the slot 312 of the body 31. The protruding parts 33 are transversely formed separately on the outside wall of the body 31 and selectively slide into the lock holes 133 of the sleeve 10.

The high pressure air source 40 is mounted slidably in the body 31 of the barrel 30. In one embodiment, a collar 41 is mounted around the high pressure air source 40 and is against the inside wall of the body 31 to keep the high pressure air source 40 to slide along a central axis.

With reference to FIGS. 2, 4, 6 and 7, the driven unit 50 is mounted slidably in the barrel 30, is attached to the high-pressure air source 40, is selectively held by the limiting unit 13 and is selectively actuated by the actuating unit 20 to slide toward the second end of the barrel 30. In one embodiment, the driven unit 50 may comprise a piston 51 and a cam 52. The piston 51 is attached to the high-pressure air source 40. The cam 52 is mounted around the piston 51, selectively presses against the resilient element 22 and has an annular wall, multiple protrusions 521 and a central bump 522. The protrusions 521 are transversely formed separately on the annular wall of the cam 52. Each protrusion 521 selectively slides in one of the passage 132 of the sleeve 10 and selectively abuts against an end of one of the stop 131 of the sleeve 10. Each protrusion 521 has an inclined side 521a and an upright side 521b. The inclined side 521a of the protrusion 521 selectively abuts against the inclined surface 212b of one of the claws 212 of the actuating cap 21. The central bump 522 is formed longitudinally on the cam 52 and may be selectively protrude in one end of the resilient element 22.

With reference to FIG. 6, when the driven unit 50 and the high pressure air source 40 are not mounted into the second opening 12 of the sleeve 10 yet, the resilient element 22 is released. The high-pressure air source 40 is held by the piston 51 and is away from the piercing needle 321.

Figure 8:
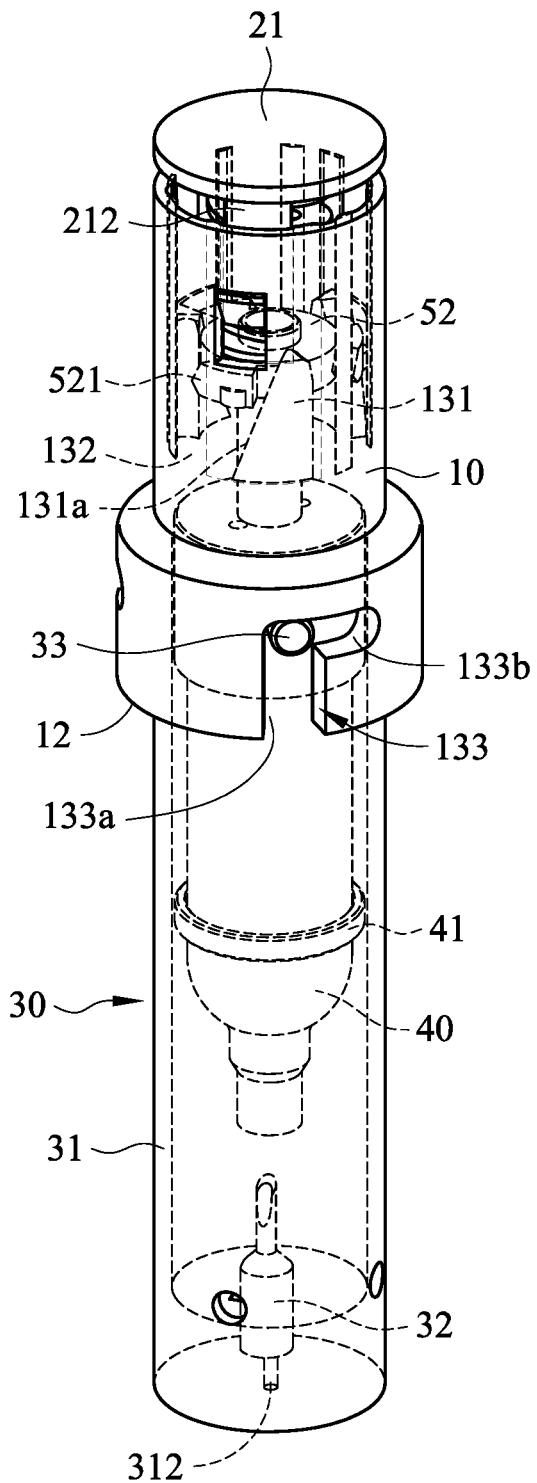
FIG. 8 is an operational perspective view of the automatic injection device for fluid in FIG. 1, showing that the barrel is inserted into the sleeve.
Figure 9:
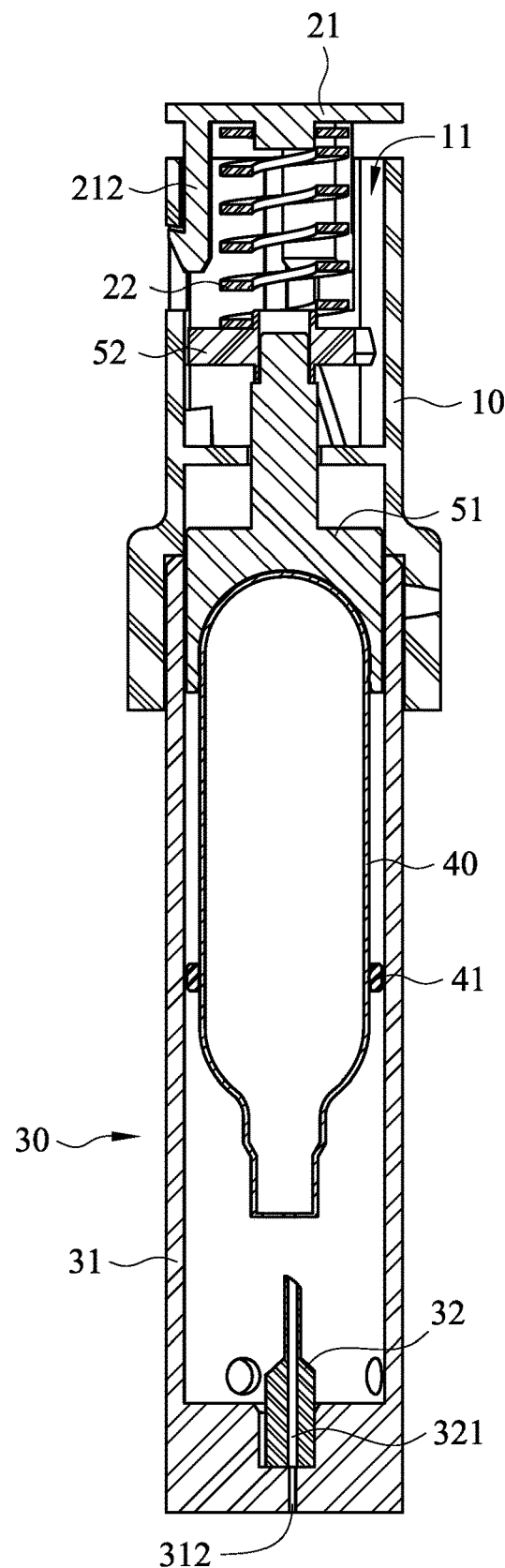
FIG. 9 is an operational side view in partial section of the automatic injection device for fluid in FIG. 1, showing that the barrel is inserted into the sleeve.

With reference to FIGS. 8 and 9, then the barrel 30 is pushed into the second opening 12 of the sleeve 10 to insert the driven unit 50 and the high pressure air source 40 into the second opening 12 of the sleeve 10. The protruding parts 33 of the barrel 30 respectively slide into the longitudinal parts 133a of the lock holes 133 of the sleeve 10. The protrusions 521 of the cam 52 respectively slide along the passages 132 of the sleeve 10 and respectively abuts against the claws 212 of the actuating cap 21 to push the actuating cap 21 to move toward the first end opening 11 of the sleeve 10. The upright sides 521b of the protrusions 521 respectively slide along the inclined sides 131a of the stops 131 of the sleeve 10.

Figure 10:
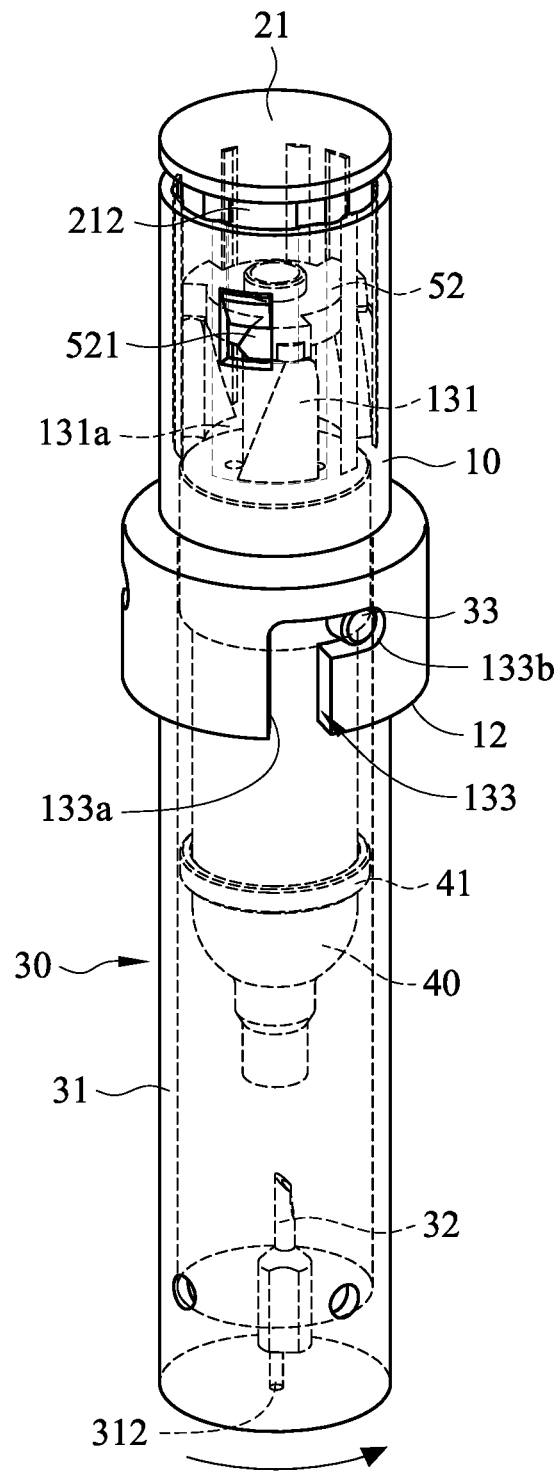
FIG. 10 is an operational perspective view of the automatic injection device for fluid in FIG. 1, showing that the barrel is rotated.
Figure 11:
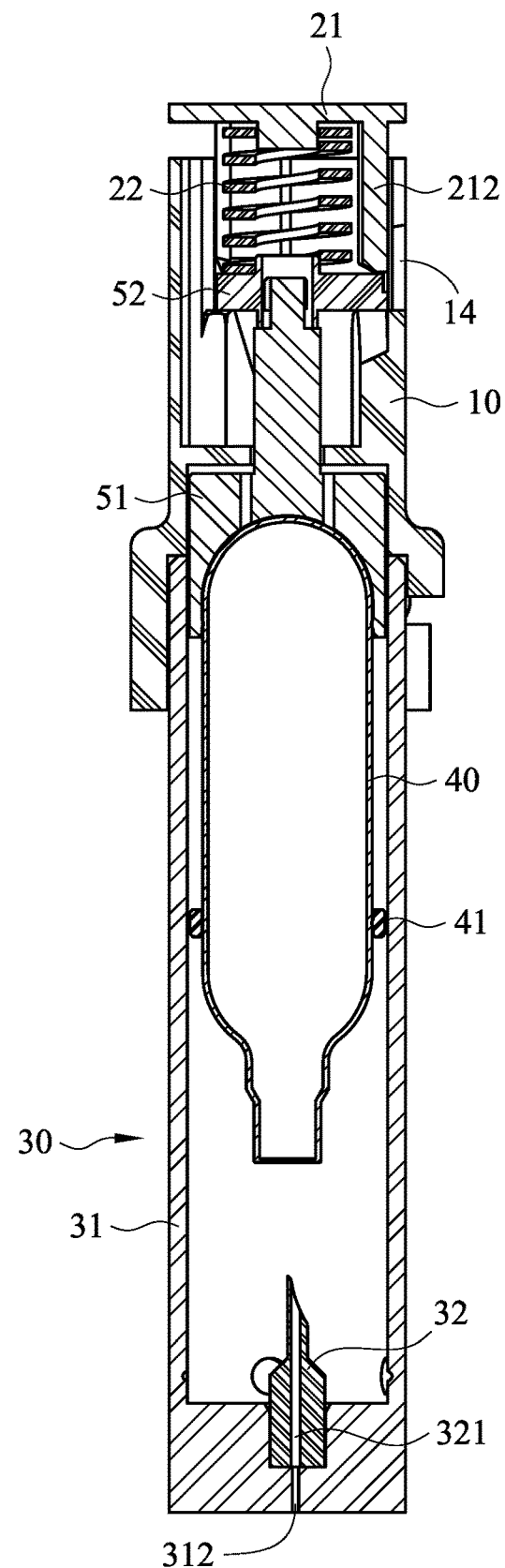
FIG. 11 is an operational side view in partial section of the automatic injection device for fluid in FIG. 1, showing that the barrel is rotated.

With reference to FIGS. 10 and 11, the barrel 30 is rotated after the protruding parts 33 of the barrel 30 respectively slide to the ends of the longitudinal parts 133a of the lock holes 133 of the sleeve 10. When the barrel 30 is rotated, the protruding parts 33 respectively slide along the lateral parts 133b of the lock holes 133 of the sleeve 10. The protrusions 521 of the cam 52 respectively slide along the inclined sides 131a of the stop 131 to constantly push the actuating cap 21 to move toward the first end opening 11 of the sleeve 10. Since the sliding route of the tabs 212c of the claws 212 of the actuating cap 21 are limited by the windows 14 of the sleeve 10, the actuating cap 21 is stopped from moving toward the first end opening 11 of the sleeve 10 by the windows 14 of the sleeve 10. Then the protrusions 521 of the cam 52 respectively slide along the inclined sides 131a of the stop 131 to leave the claws 212 of the actuating cap 21 and to compress the resilient element 22. When the protruding parts 33 of the barrel 30 respectively slide to the ends of the lateral parts 133b of the lock holes 133 of the sleeve 10, the protrusions 521 of the cam 52 respectively slide on ends of the stops 131 and the inclined sides 521a of the protrusions 521 respectively abut against the inclined surfaces 212b of the claws 212 of the actuating cap 21. Since the protrusions 521 of the cam 52 are stopped by the ends of the stops 131, the cam 52 along with the piston 51 and the high-pressure air source 40 are stopped from moving toward the second end opening 12 even the resilient element 22 pushes.

Figure 12:
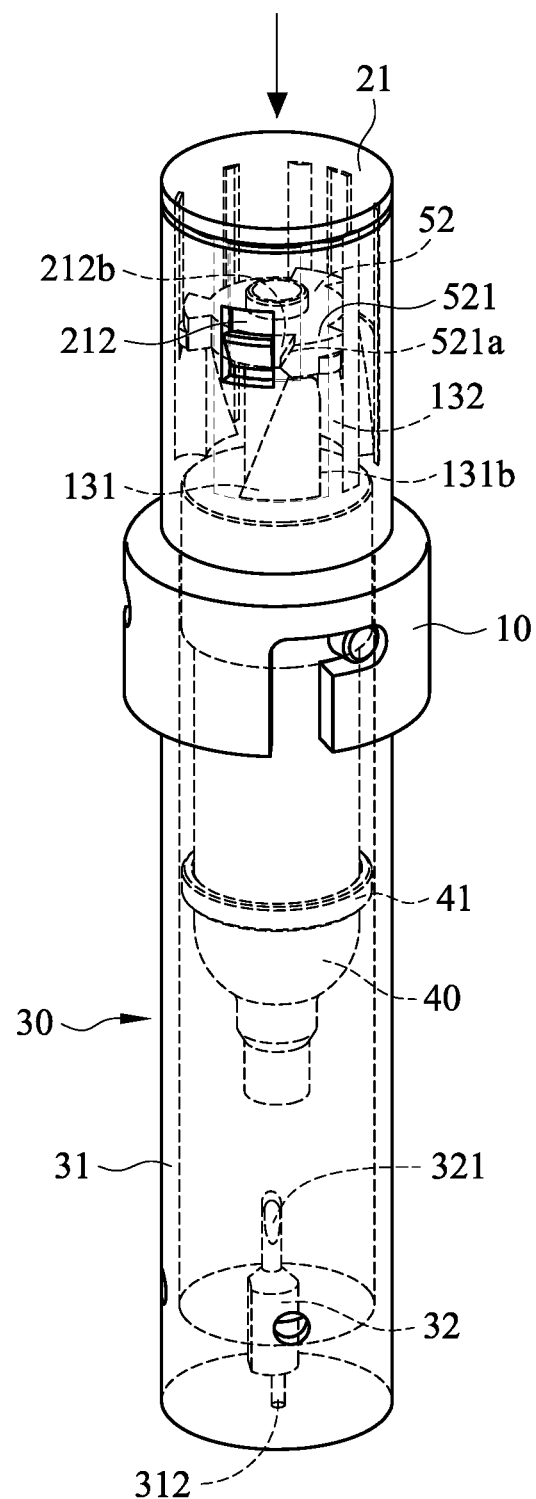
FIG. 12 is an operational perspective view of the automatic injection device for fluid in FIG. 1, showing that the actuating cap is pressed.
Figure 13:
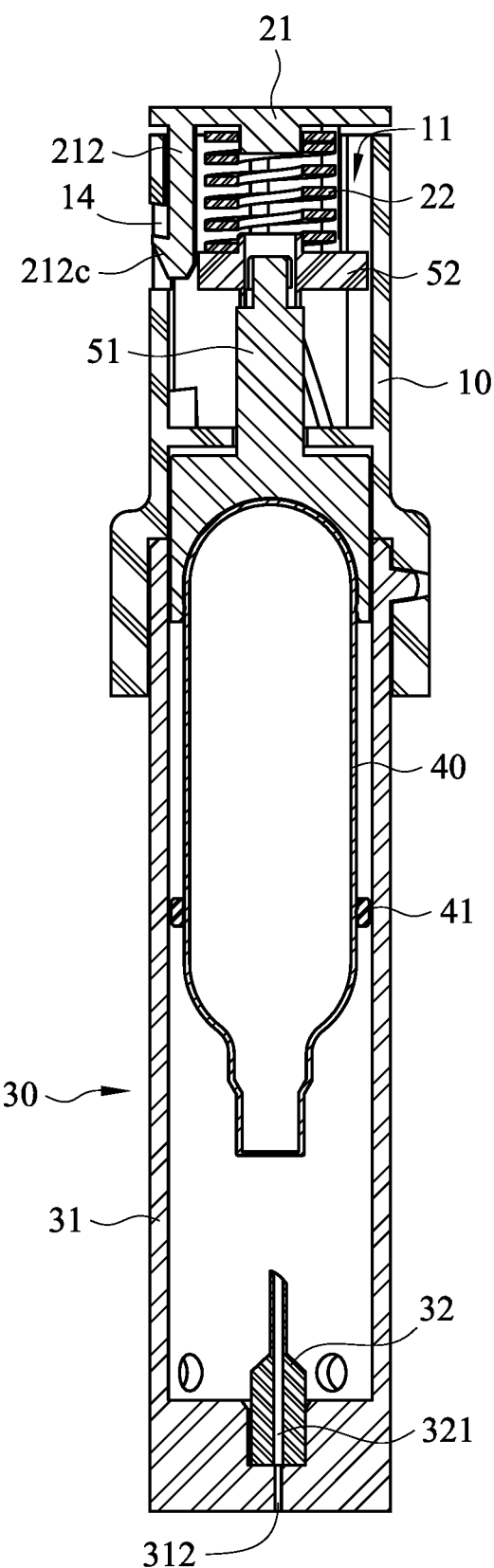
FIG. 13 is an operational side view in partial section of the automatic injection device for fluid in FIG. 1, showing that the actuating cap is pressed.

With reference to FIGS. 12 and 13, the user press the actuating cap 21 when the user needs to release the high-pressure air in the high-pressure air source 40. When the actuating cap 21 is pressed into the first end opening 11 of the sleeve 10, the inclined surfaces 212b of the claws 212 of the actuating cap 21 respectively pushes the inclined sides 521a of the protrusions 521 of the cam 52 so that the cam 52 is forced to rotate. The resilient element 22 is kept compressed between the actuating cap 21 and the cam 52.

Figure 14:
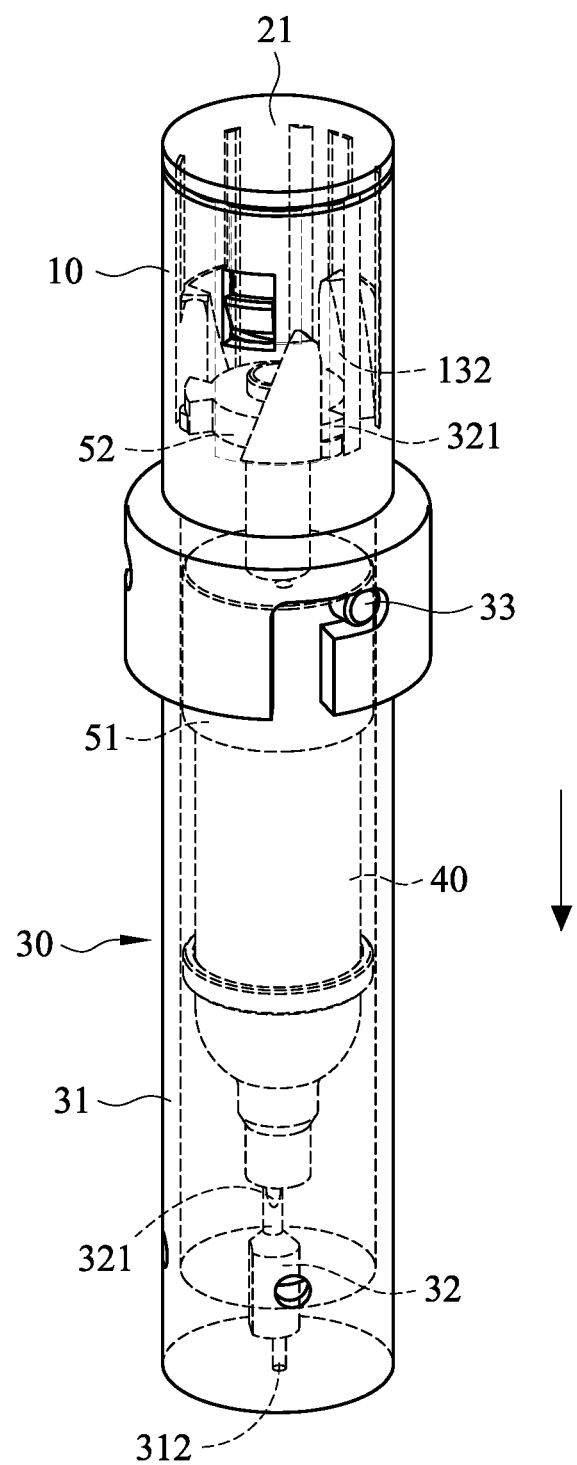
FIG. 14 is an operational perspective view of the automatic injection device for fluid in FIG. 1, showing that the cam with the high-pressure air source slide toward the second end of the barrel.
Figure 15:
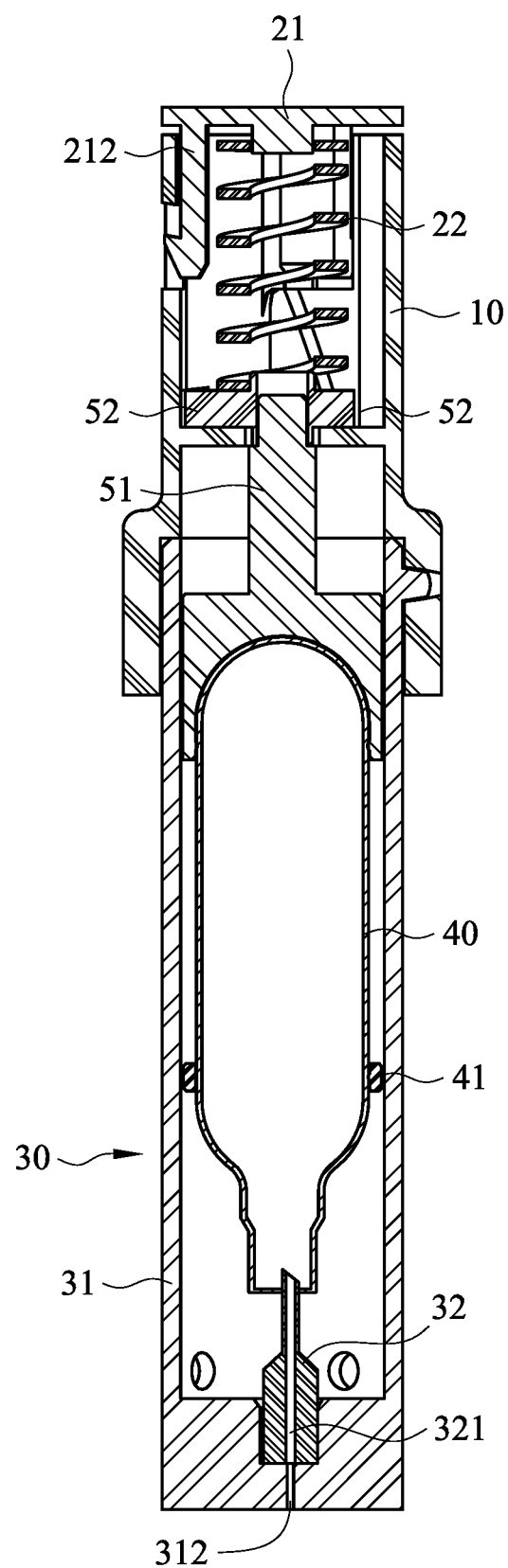
FIG. 15 is an operational side view in partial section of the automatic injection device for fluid in FIG. 1, showing that the cam with the high-pressure air source slide toward the second end of the barrel.

With reference to FIGS. 14 and 15, the cam 52 is forced to rotate until the protrusions 521 respectively align with the passages 132 of the sleeve 10. Since the stops 131 of the sleeve 10 no longer abut the protrusions 521 of the cam 52 when the protrusions 521 respectively align with the passages 132 of the sleeve 10, the resilient force of the resilient element 22 pushes the cam 52 to move toward the second end opening 12 of the sleeve 10. The barrel 30 is not move toward the second end opening 12 of the sleeve 10 since the protruding parts 33 are respectively located in the lateral parts 133b of the lock holes 133 of the sleeve 10. Therefore, the cam 52 along with the piston 51 and the high-pressure air source 40 are pushed toward the second end opening 12 of the sleeve 10 and toward the second end of the body 31 of the barrel 30 until an end of the high-pressure air source 40 hits the piercing needle 32. Then the end of the high-pressure air source 40 is punctured through by the piercing needle 32 to release the high-pressure air in the high-pressure air source 40 through the central hole 321 of the piercing needle 32 and the slot 312 of the body 31 of the barrel 30 so that the fluid in the associate device is injected to the subject via the pneumatic force of the high-pressure air.

Figure 16:
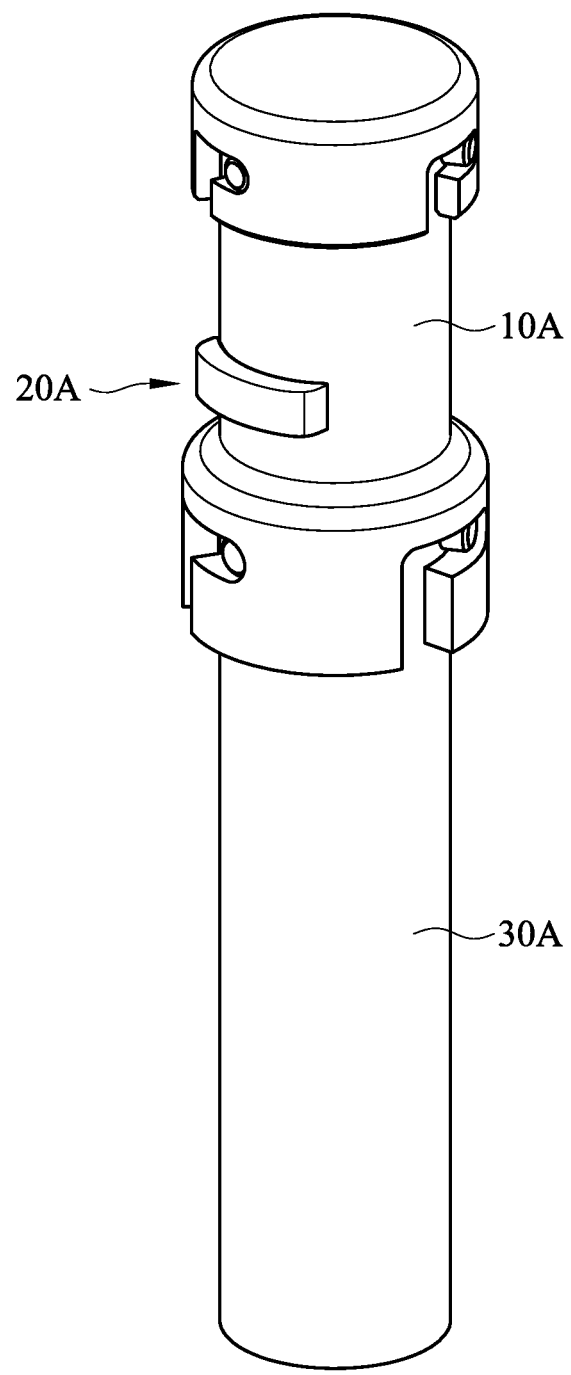
FIG. 16 is a perspective view of another embodiment of an automatic injection device for fluid in accordance with the present invention.
Figure 17:
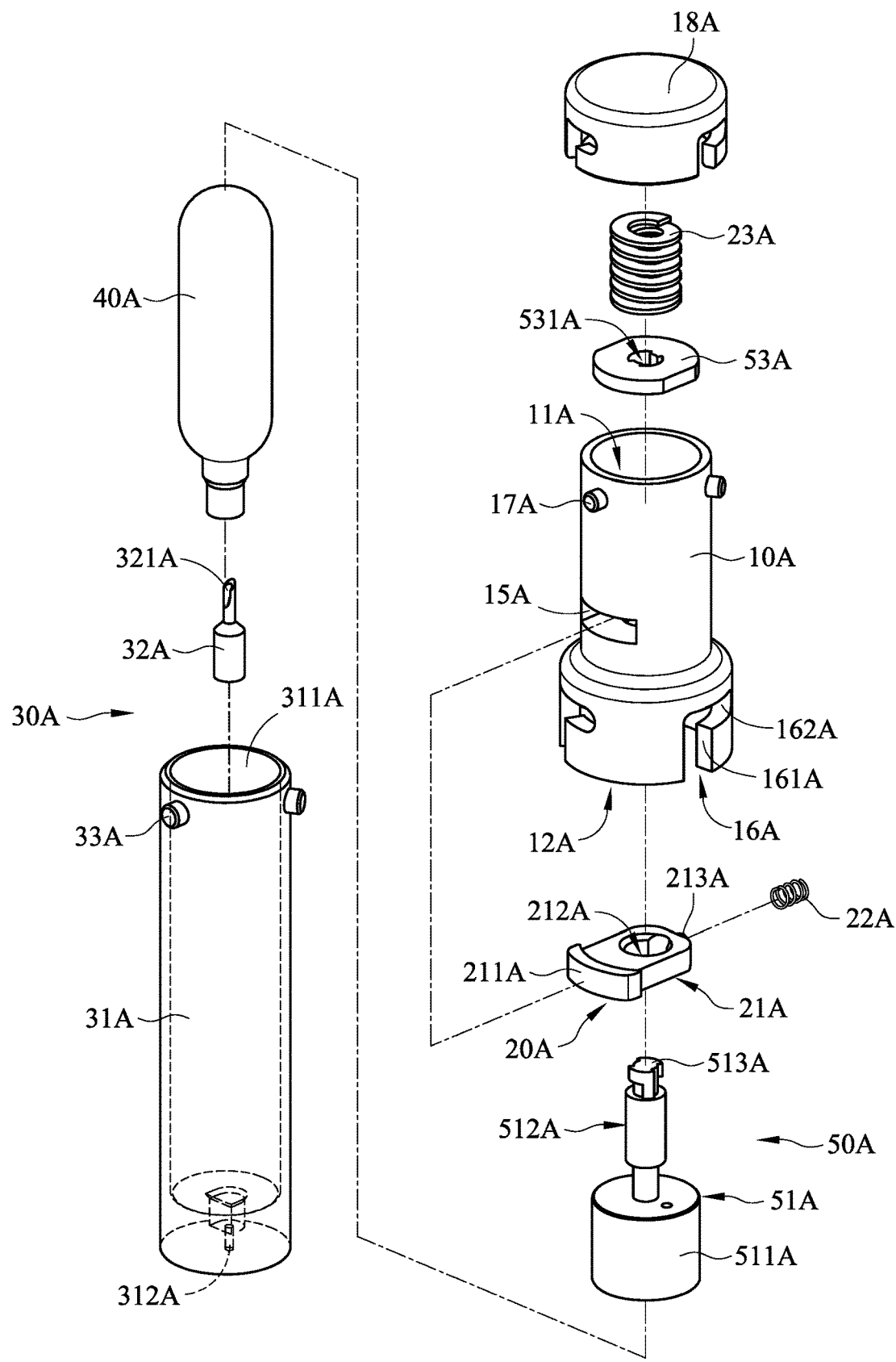
FIG. 17 is an exploded perspective view of the automatic injection device for fluid in FIG. 16.

With reference to FIGS. 16 and 17, another embodiment of an automatic injection device for fluid in accordance with the present invention comprises a sleeve 10A, an actuating unit 20A, a barrel 30A, a high-pressure air source 40A and a driven unit 50A.

The sleeve 10A is hollow and has an inside wall, an outside wall, a first end opening 11A, a second end opening 12A, a side hole 15A, multiple lock holes 16A, multiple lock protrusions 17A and a cap 18A. The side hole 15A is formed transversely through the sleeve 10. The lock holes 16A are formed transversely through the sleeve 10A. Each lock hole 16A has a longitudinal part 161A and a lateral part 162A communicating with the longitudinal part 161A. The longitudinal part 161A of each lock hole 16A communicates with the second end opening 12A of the sleeve 10A. The lock protrusions 17A are transversely formed separately on the outside wall of the sleeve 10A. The cap 18A is mounted on the first end opening 11A of the sleeve 10A and may be held by the lock protrusions 17A.

Figure 18:
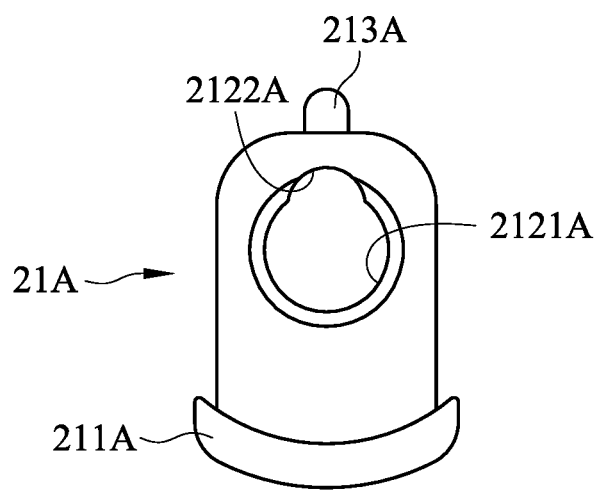
FIG. 18 is a top view of an actuating washer of the automatic injection device for fluid in FIG. 16.

With reference to FIGS. 16 to 18, the actuating unit 20A is mounted in the sleeve 10A. The actuating unit 20A has an actuating washer 21A, a resisting resilient element 22A and an actuating resilient element 23A. The actuating washer 21A is mounted slidably through the side hole 15A of the sleeve 10A and has a distal end, a proximal end, an enlarged head 211A, a limiting unit and a mounting tag 213A. The enlarged head 211A is formed on the distal end of the actuating washer 21A and protrudes out of the side hole 15A. The limiting unit is defined in the sleeve 10A and may be a through hole 212A formed through the actuating washer 21A, located in the sleeve 10A and having a larger part 2121A and a smaller part 2122A. The larger part 2121A of the through hole 212A is near the distal end while the smaller part 2122A is near the proximal end. The larger part 2121A and the smaller part 2122A communicate with each other and an inner diameter of the larger part 2121A is larger than an inner diameter of the smaller part 2122A. The mounting tag 213A is formed on the proximal end. The resisting resilient element 22A is mounted around the mounting tag 213A and is pressed between the proximal end of the actuating washer 21A and the inside wall of the sleeve 10A. The actuating resilient element 23A is mounted in the sleeve 10A and is pressed against the cap 18A.

With reference to FIGS. 16 and 17, the barrel 30A is selectively held on the second end opening 12A of the sleeve 10A and may comprise a body 31A, a piercing needle 32A and multiple protruding parts 33A. The body 31A is hollow and has an inside wall, an outside wall, a first end opening 311A, a second end and a slot 312A. The slot 312A is formed through the second end of the body 31A. The piercing needle 32A is attached to the second end of the body 31A and may have a central hole 321A communicating with the slot 312A of the body 31A. The protruding parts 33A are transversely formed separately on the outside wall of the body 31A and selectively slide into the lock holes 16A of the sleeve 10A.

The high pressure air source 40A is mounted slidably in the body 31A of the barrel 30A.

Figure 19:
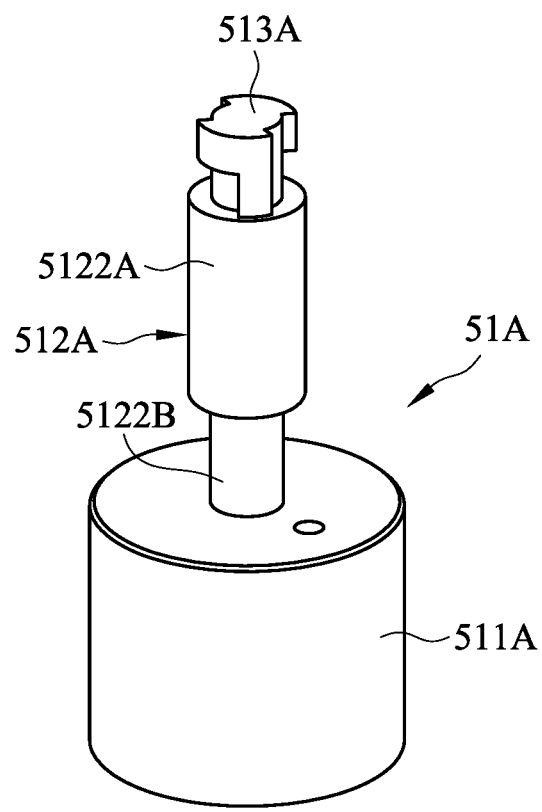
FIG. 19 is a perspective view of a piston of the automatic injection device for fluid in FIG. 16.
Figure 20:
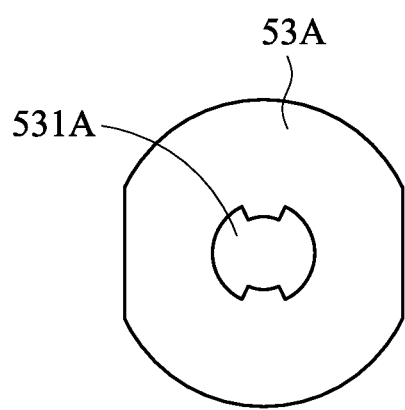
FIG. 20 is a top view of a washer of the automatic injection device for fluid in FIG. 16.

With reference to FIGS. 17, 19 and 20, the driven unit 50A is mounted slidably in the barrel 30A is attached to the high-pressure air source 40A, is selectively held by the limiting unit and is selectively actuated by the actuating unit 20A to slide toward the second end of the barrel 30A. In one embodiment, the driven unit 50 may comprise a piston 51A and a washer 53A. The piston 51A is attached to the high-pressure air source 40A and has a crown 511A, a shaft 512A and a cam 513A. The crown 511A is attached to the high-pressure air source 40A. The shaft 512A is formed longitudinally on the crown 511A and has a thinner segment 5121A and a thicker segment 5122A. The thinner segment 5121A is formed longitudinally on the crown 211A and selectively aligns with the smaller part 2122A of the through hole 212A of the actuating washer 21A. The thicker segment 5122A is formed longitudinally on, aligns with the thinner segment 5121A and selectively aligns with the larger part 2121A of the through hole 212A of the actuating washer 21A. The cam 513A is formed on an end of the thicker segment 5122A. The washer 53A is secured on the piston 51A via a cam hole 531A penetrated by the cam.

Figure 21:
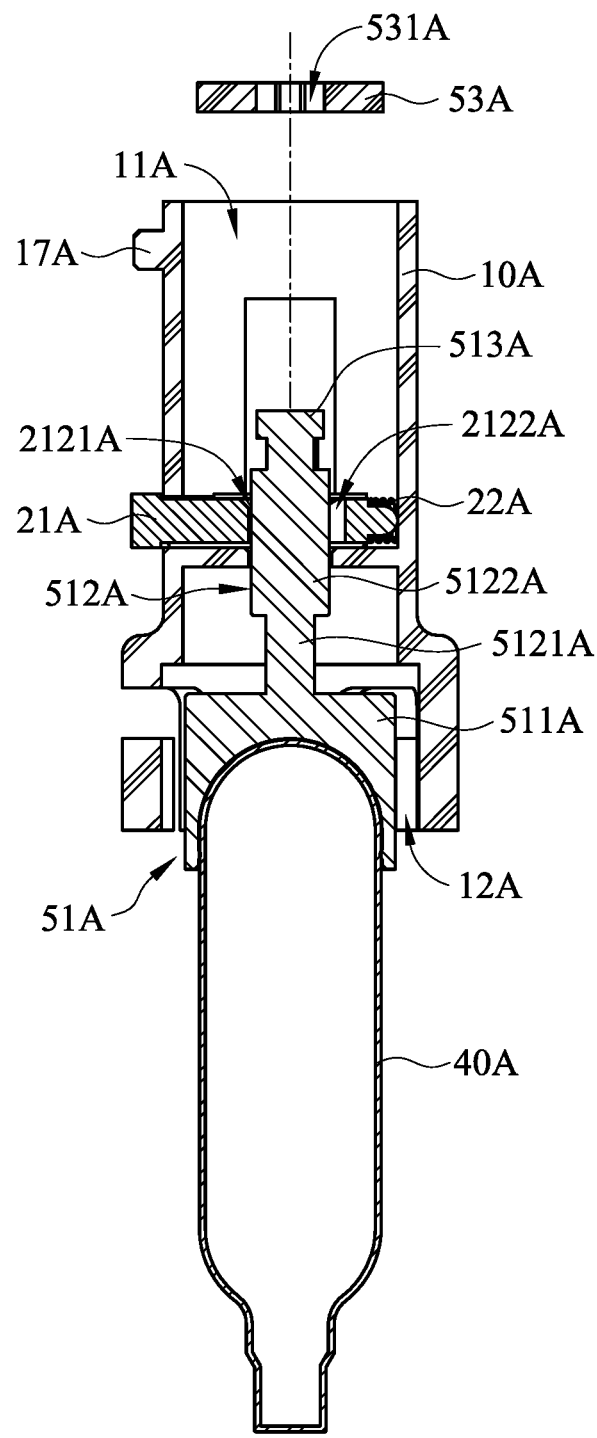
FIG. 21 is an operational side view in partial section of the automatic injection device for fluid in FIG. 16, showing that the piston and a high-pressure air source is mounted into a sleeve.
Figure 22:
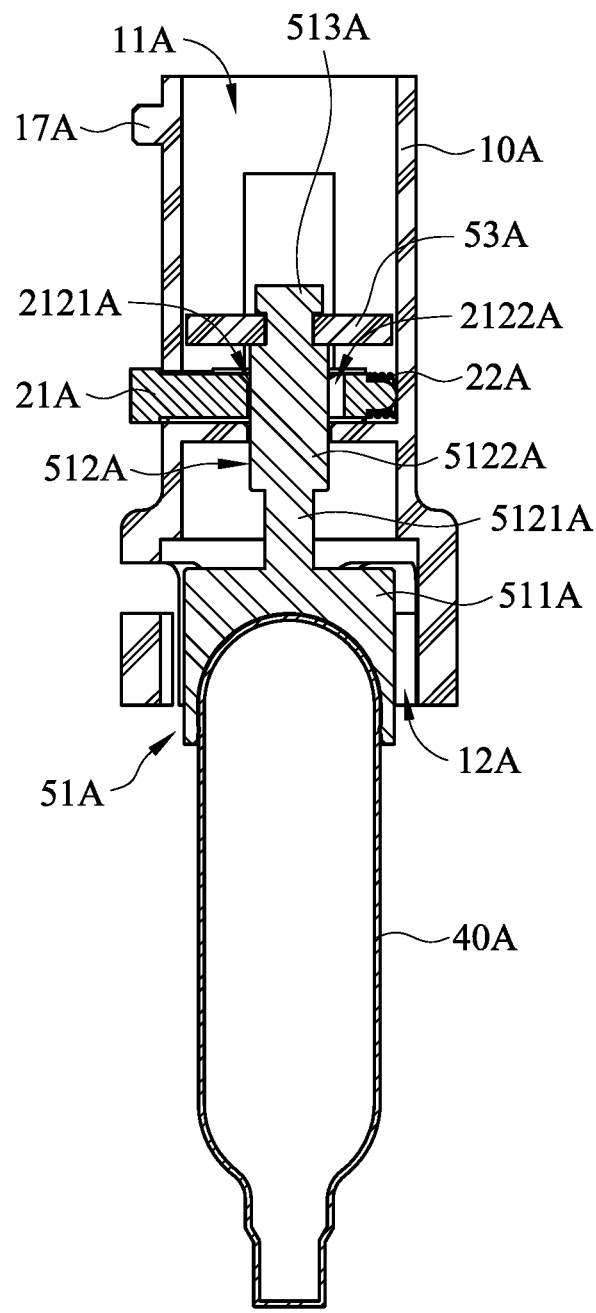
FIG. 22 is an operational side view in partial section of the automatic injection device for fluid in FIG. 16, showing that the washer is mounted into the sleeve.

With reference to FIGS. 21 and 22, the high-pressure air source 40A is attached to the crown 511A of the piston 51A. The piston 51A with the high-pressure air source 40A is mounted into the sleeve 10A through the second end opening 12A. The thicker segment 5122A of the shaft 512A of the piston 51A is mounted in the larger part 2121A of the through hole 212A of the actuating washer 21A to keep the actuating washer 21A from pushing outward by the resisting resilient element 22A. The washer 53A is mounted into the sleeve 10A through the first end opening 11A and aligns the cam hole 531A with the cam 513A to mounted around the piston 51A. Then the piston 51A is rotated to misalign the cam 513A and th cam hole 531A so that the washer 53A is secured around the piston 51A.

Figure 23:
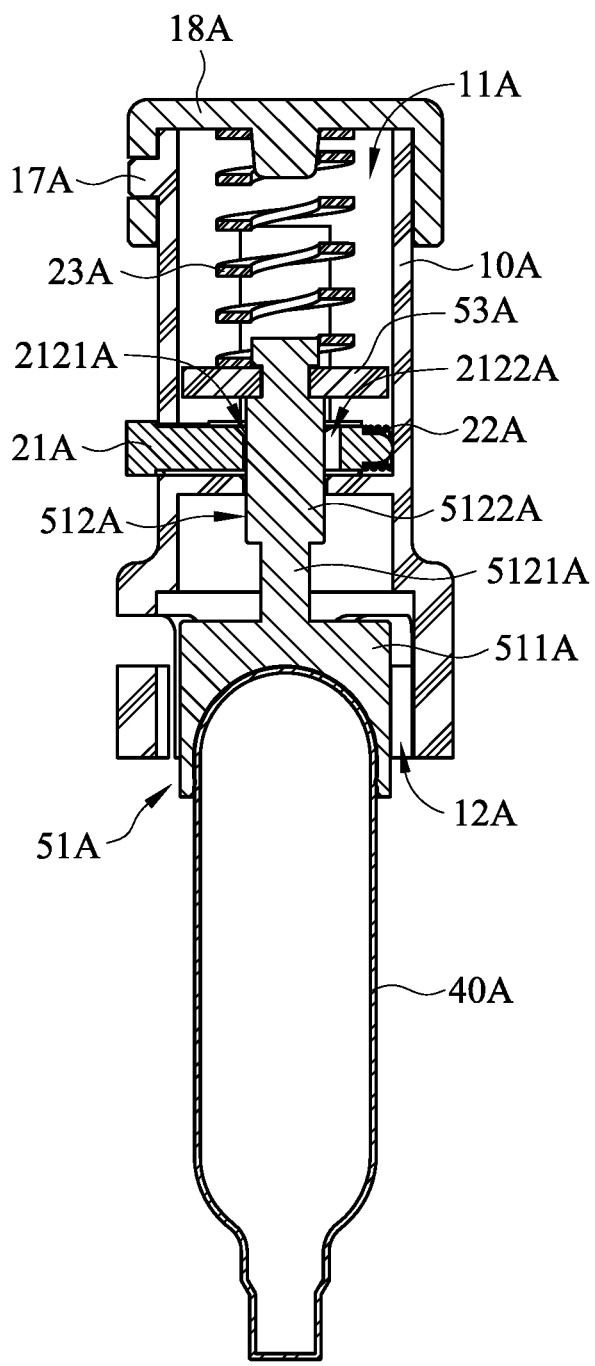
FIG. 23 is an operational side view in partial section of the automatic injection device for fluid in FIG. 16, showing that an actuating resilient element is mounted in the sleeve.

With reference to FIG. 23, the actuating resilient element 23A and the cap 18A are mounted into the first end opening 11A. The actuating resilient element 23A is clamped between the washer 53A and the cap 18A.

Figure 24:
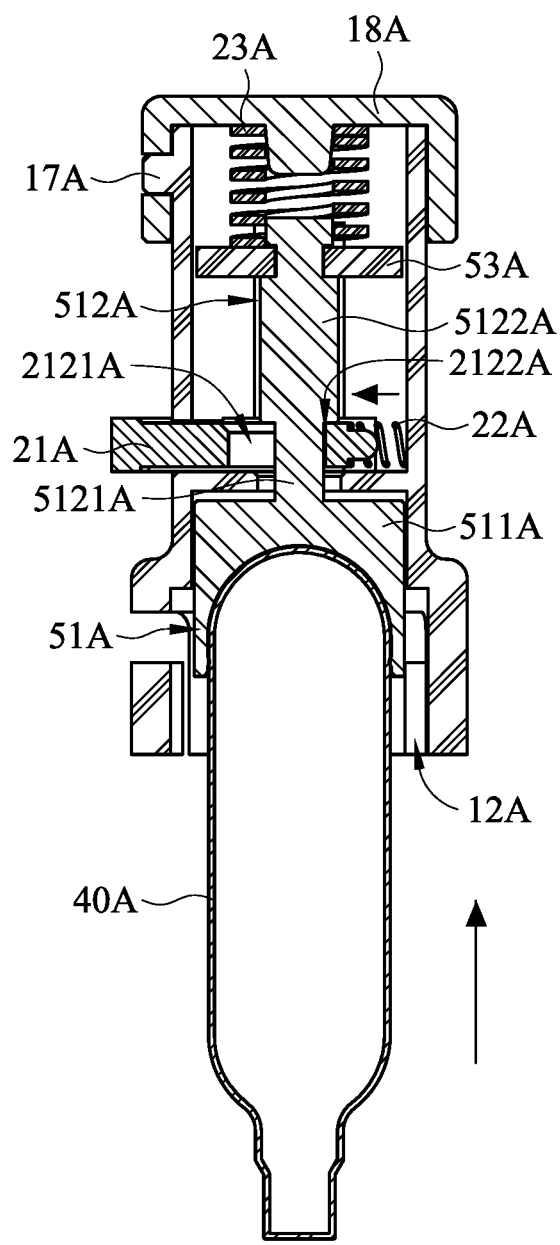
FIG. 24 is an operational side view in partial section of the automatic injection device for fluid in FIG. 16, showing that the piston and the high-pressure air source are pushed upward to be locked in position.

With reference to FIG. 24, the high-pressure air source 40A is pushed upward to force the piston 51A to move upward. Then the shaft 512A is moved upward and the thicker segment 5121A passes through the through hole 212A of the actuating washer 21A. When the thicker segment 5122A leaves the through hole 212A and the thinner segment 5121A reaches the through hole 212A, the resisting resilient element 22A releases its resilient force to push the actuating washer 21A to move outward. Then the smaller part 2122A of the through hole 212A aligns with the thinner segment 5121A of the shaft 512A to keep the thicker segment 5122A of the shaft 512A from moving into the through hole 212A so that the thicker segment 5122A abuts against the upper surface of the actuating washer 21A. In the mean time, the actuating resilient element 22A is compressed by the washer 53A to restore the resilient force.

Since the thicker segment 5122A of the shaft 512A abuts against the upper surface of the actuating washer 21A, the shaft 212A is kept from moving downward even though the actuating resilient element 22A presses against the washer 53A.

Figure 25:
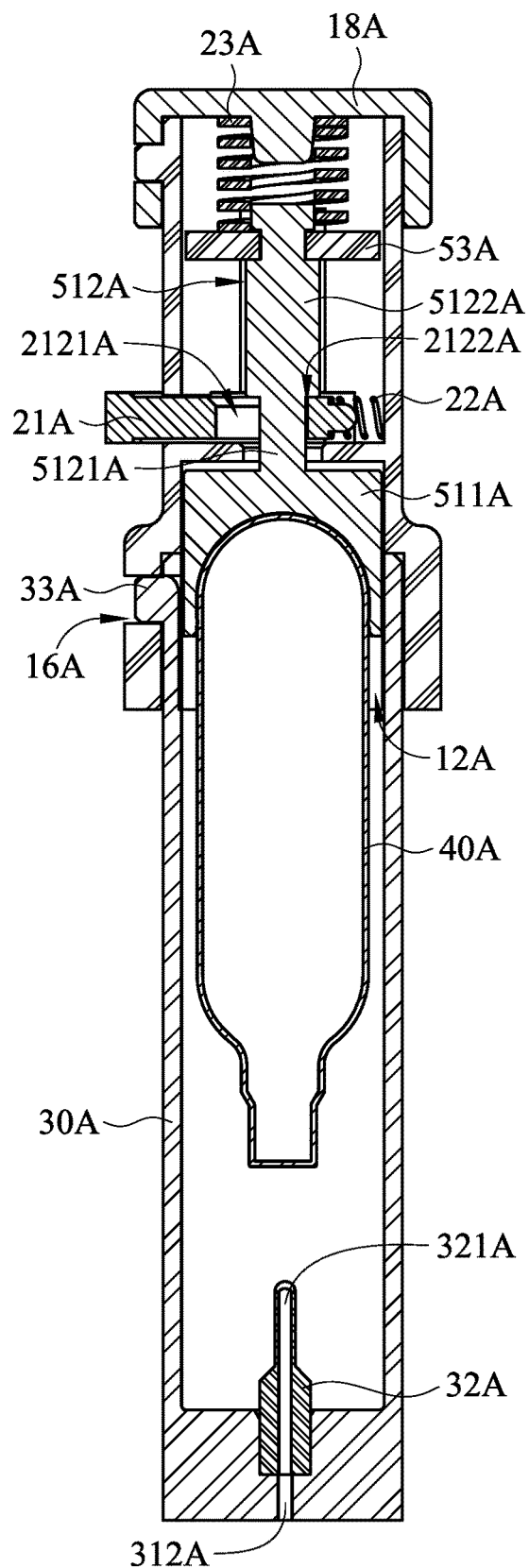
FIG. 25 is an operational side view in partial section of the automatic injection device for fluid in FIG. 16, showing that a barrel is mounted around the high-pressure air source.

With reference to FIG. 25, the barrel 30A is mounted into the second end opening 12A of the sleeve 10A to be mounted around the high-pressure source 40A. The barrel 30A is rotated to engage the protruding parts 33A in the lock holes 16A so that the barrel 30A is secured around the high-pressure air source 40A.

Figure 26:
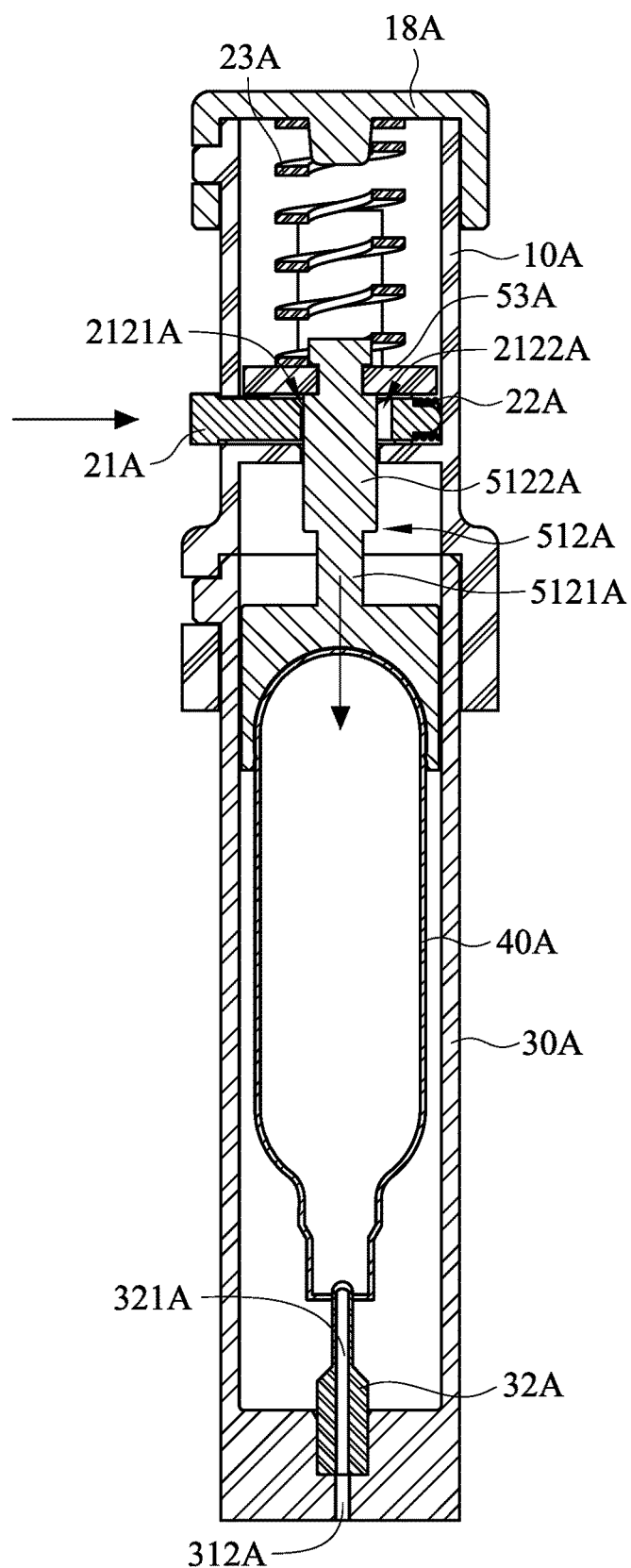
FIG. 26 is an operational side view in partial section of the automatic injection device for fluid in FIG. 16, showing that an actuating unit is actuated to push the piston and the high-pressure air source to move downward.

With reference to FIG. 26, the user press the actuating washer 21A when the user needs to release the high-pressure air in the high-pressure air source 40A. The actuating washer 21A is pressed into the sleeve 10A to align the larger part 2121A of the through hole 212A with the thicker segment 5122A of the shaft 512A so that the thicker segment 5122A is allowed to pass through the through hole 212A again. Then the actuating resilient element 23A releases its resilient force to push the shaft 512A to move downward with the thicker segment 5122A of the shaft 512A passing through the larger part 2121A of the through hole 212A. Thus, the piston 51A along with the high-pressure air source 40A are pushed toward the second end opening 12A of the sleeve 10A and toward the second end of the body 31A of the barrel 30A until an end of the high-pressure air source 40A hits the piercing needle 32A. Then the end of the high-pressure air source 40A is punctured through by the piercing needle 32A to release the high-pressure air in the high-pressure air source 40A through the central hole 321A of the piercing needle 32A and the slot 312A of the body 31A of the barrel 30 so that the fluid in the associate device is injected to the subject via the pneumatic force of the high-pressure air.

The advantages of the automatic injection device for fluid as described are recited as follow. With the cooperation of the driven unit 50, 50A and the actuating unit 20, 20A, the high-pressure air in the high-pressure air source 40, 40A is easily released by actuate the actuating unit 20, 20A without additional hand tools. Therefore, the user can use the automatic injection device for fluid as described to inject the fluid in the associate device conveniently.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. An automatic injection device for fluid comprising:
    a hollow sleeve and having
        a first end opening;
        a second end opening;
        a side hole formed transversely through the sleeve; and
        a cap mounted on the first end opening of the sleeve;
    an actuating unit mounted in the sleeve and having
        an actuating washer mounted slidably through the side hole of the sleeve and having a distal end and a proximal end;
        a resisting resilient element clamped between an inside wall of the sleeve and the proximal end of the actuating washer; and
        an actuating resilient element mounted in the sleeve and pressed against the cap;
    a barrel selectively held on the second end opening of the sleeve and having
        a body having a first end opening and a second end;
        a piercing needle attached to the second end of the body;
    a high-pressure air source mounted slidably in the body of the barrel; and
    a driven unit mounted slidably in the barrel, attached to the high-pressure air source, selectively held by a limiting unit, selectively actuated by the actuating unit to slide toward the second end of the barrel and selectively pushing the high-pressure air source to slide toward the second end of the barrel, wherein
    the limiting unit is a through hole formed through the actuating washer, located in the sleeve and having a larger part near the distal end of the actuating washer and a smaller part near the proximal end;
    the driven unit comprises
        a piston attached to the high-pressure air source and having a shaft having
            a thinner segment selectively aligning with the smaller part of the through hole; and
            a thicker segment is formed longitudinally on the thinner segment and selectively aligning with the larger part; and
    the actuating resilient element is clamped between the piston and the cap.

2. The automatic injection device for fluid as claimed in claim 1, wherein
    the driven unit comprises a washer secured on the piston; and
    the actuating resilient element is clamped between the washer and the cap.

3. The automatic injection device for fluid as claimed in claim 2, wherein
    the piston has a cam formed on an end of the thicker segment; and
    the washer of the driven unit secured on the piston via a cam hole penetrated by the cam.

4. The automatic injection device for fluid as claimed in claim 1, wherein
    the actuating washer has a mounting tag formed on the proximal end of the actuating washer; and
    the resisting resilient element is mounted around the mounting tag.

5. The automatic injection device for fluid as claimed in claim 1, wherein
    the piston has a crown attached to the high-pressure air source; and
    the thinner segment of the shaft is formed longitudinally on the crown.

6. The automatic injection device for fluid as claimed in claim 1, wherein
    the body of the barrel has a slot formed through the second end of the body; and
    the piercing needle has a central hole communicating with the slot of the body.

7. The automatic injection device for fluid as claimed in claim 1, wherein the resilient element is a spring.

\* \* \* \* \*